United States Patent [19]
Laughlin

[11] Patent Number: 5,159,938
[45] Date of Patent: Nov. 3, 1992

[54] EYE SHIELD

[76] Inventor: Patrick E. Laughlin, 1191 Beechwood Dr., Green Bay, Wis. 54303

[21] Appl. No.: 750,521

[22] Filed: Aug. 27, 1991

[51] Int. Cl.$^5$ .............................................. A61F 9/00
[52] U.S. Cl. .................................... 128/858; 128/857; 128/207.11; 128/207.13
[58] Field of Search ............. 128/858, 205.25, 206.21, 128/206.23, 206.26, 207.11, 207.13, 857, 207.18

[56] References Cited

U.S. PATENT DOCUMENTS

| | | | |
|---|---|---|---|
| 2,372,834 | 4/1945 | Kish | 128/207.13 X |
| 2,462,005 | 2/1949 | Schauweker | 128/207.11 |
| 4,157,090 | 6/1979 | Phillips | 128/207.11 |
| 4,846,170 | 7/1989 | McAnalley et al. | 128/207.13 |
| 4,969,473 | 11/1990 | Bothwell | 128/858 |
| 5,018,519 | 5/1991 | Brown | 128/206.21 X |

FOREIGN PATENT DOCUMENTS 304641  3/1989  European Pat. Off. ....... 128/206.26

Primary Examiner—Robert A. Hafer
Assistant Examiner—Kerry Owens
Attorney, Agent, or Firm—Russell L. Johnson

[57] ABSTRACT

This invention is a protective eye shield that indexes to an inhalation gas providing nose hood and the hood's hoses to provide secure eye protection to a patient wearing such a hood during the performance of dental procedures. The shield further indexes to the temples and forehead of the wearer to provide secure and comfortable positioning of the shield. The shield cooperates with the inhalation hood in providing a shield against materials reaching the patients eyes.

8 Claims, 3 Drawing Sheets

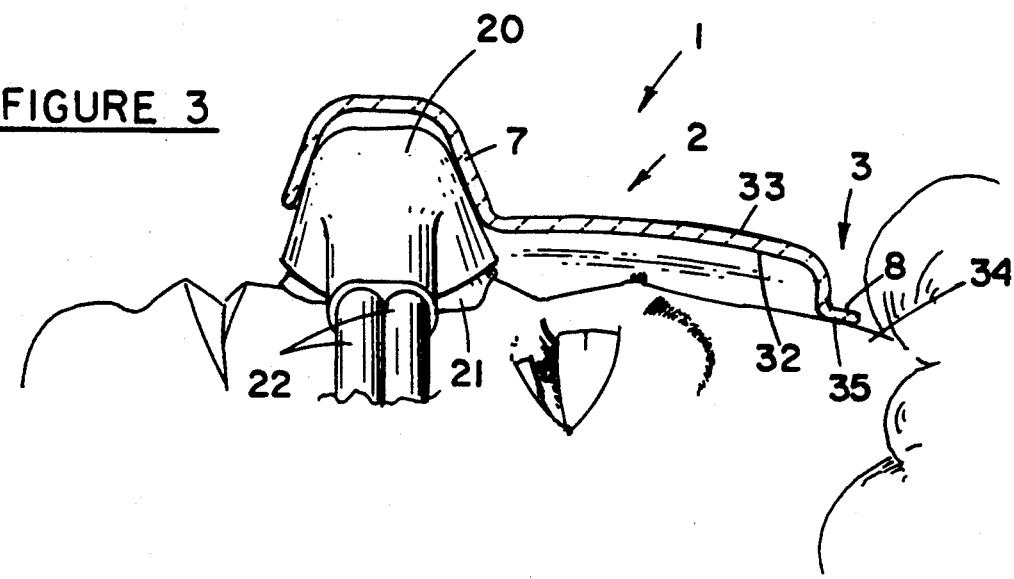
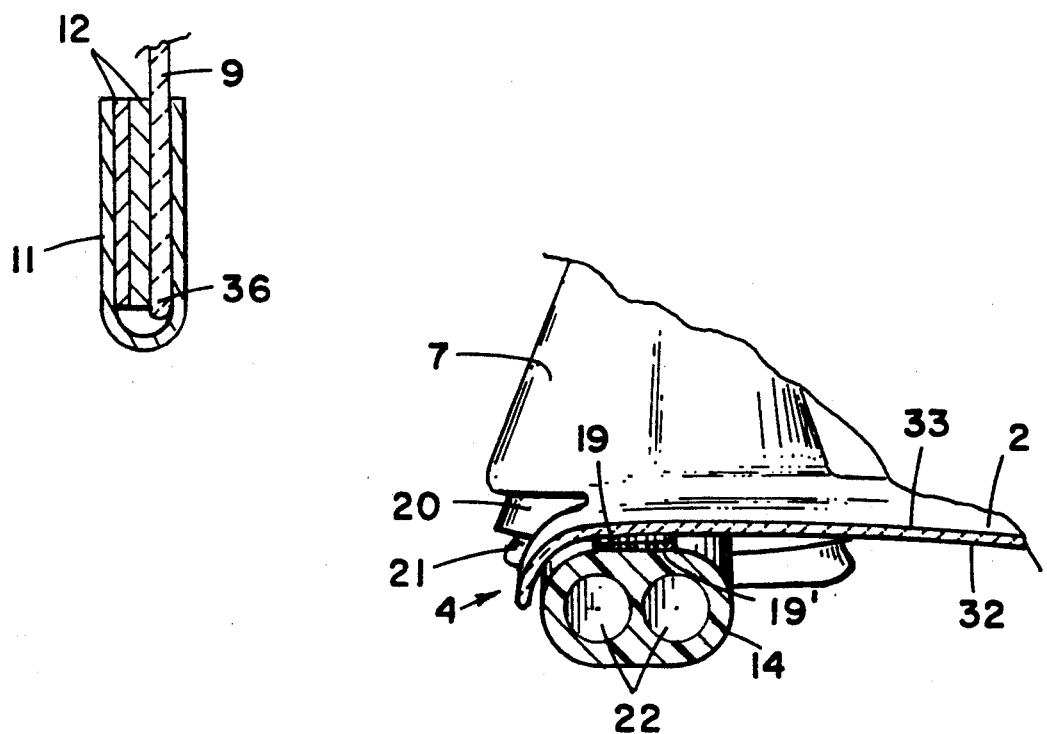

EYE SHIELD

BACKGROUND OF THE INVENTION

When performing dental procedures, using a nose hood to administer inhalation gases, there is a possibility of foreign materials reaching the patient's eyes. The nose hood has a flexible gasket that seals the hood around the nose. The areas covered by the hood would be interfered with by conventional goggles.

Access to the oral cavity is required for dental surgery, which renders prior art face shields, which cover the mouth, as unsuitable for providing eye protection during dental surgery.

In addition to materials that might reach the eyes from above, such as things dropped or spilled while working in the oral cavity, there is the risk to the eyes from matter projected from the oral cavity. Such matter might include particles dislodged during drilling or other surgical procedures, matter atomized by drilling or fluid pressure, and matter projected from the mouth by the patient. These materials would arise below a conventional eye shield and present a danger to the eyes even with the conventional shield in place due to the nose hood interfering with a proper fit of the shield.

OBJECTS

It is therefore an object of this invention to provide a protective eye shield for use on patients when the patient is wearing an inhalation-gas dispensing nose hood.

It is further an object of this invention to provide the shield described above wherein the shield provides access to the oral cavity and shields the eyes from matter arising from the oral cavity.

It is further an object of this invention to provide the shield described above wherein the shield is indexed to the nose hood and is adjustable so as to be securely and comfortably accommodating to the patients head shape.

It is further an object of this invention to provide the shield described above wherein the shield is of substantially one piece construction and of a semi-flexible transparent material that is sufficiently low in cost as to permit economical disposal of the shield after use.

Other objects of the invention will become apparent from the following descriptions, drawings and claims.

BRIEF DISCUSSION OF THE PRIOR ART

The prior art abounds in face shields that protect the eyes of the wearer. U.S. Pat. No. 4,986,282 to Stackhouse et al. teaches a shield that is typical of such devices.

The art also abounds in head gear that has protection for the eyes and a means of introducing inhalation gases to the wearer, and for expelling exhalation gases from the head gear. U.S. Pat. No. 789,145 to Derx is an early example of such a piece of head gear.

U.S. Pat. No. 3,241,155 to Phillips teaches a cushioning pad at the edge of a face shield.

U.S. Pat. No. 4,945,574 to Dagher teaches adjustable side contacts for a protective mask.

If broad language is used, it can be said that the prior art provides a number of the utilities and functions that are the same as those of the instant invention. However, the prior art does not provide an eye shield that protects the eyes of the wearer and provides access to the oral cavity when the user is wearing an inhalation gas providing nose hood.

BRIEF DESCRIPTION OF THE INVENTION

The invention, in its simplest form, is an eye shield, constructed of semi-flexible clear or tinted plastic material, and having a broad, eye protecting central span having a face side surface and an outside surface. The central span has a perimeter having a forehead edge, a nose edge, opposite the forehead edge, and a right side edge and a left side edge. The right and left side edges span the distances between the forehead edge and the nose edge, one to each side of the shield, to form a closed perimeter for the shield. A nose hood index is formed as a part of the central span near the nose edge of the shield. The nose hood index is configured so as to receive and index to an inhalation-gas dispensing hood. The forehead edge is provided with a forehead contacting surface which is configured so as to rest comfortably on a human forehead. The side edges have projecting therefrom, temple pieces which are configured to contact with and index to the temple area of a human head.

BRIEF DESCRIPTION OF THE DRAWINGS

FIG. 3 is an elevational view of the shield of FIGS. 1 and 2 in place on a patient.

FIG. 4 is a sectioned fragmentary view of a temple piece and a cushioning sleeve having an insert.

FIG. 5 is a partially sectioned elevational view of the nose edge of the shield showing a Velcro (TM) joinder means.

DETAILED DESCRIPTION OF THE INVENTION

Figure 1:
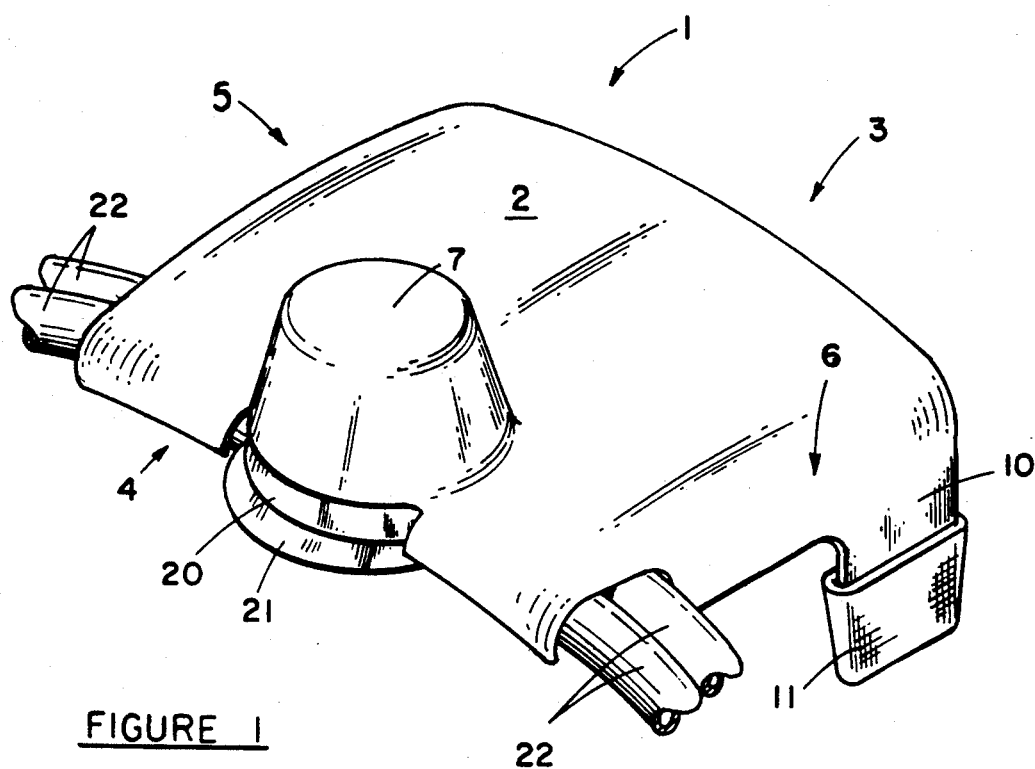
FIG. 1 is a pictorial view of the shield of this invention taken from the nose edge of the shield.
Figure 2:
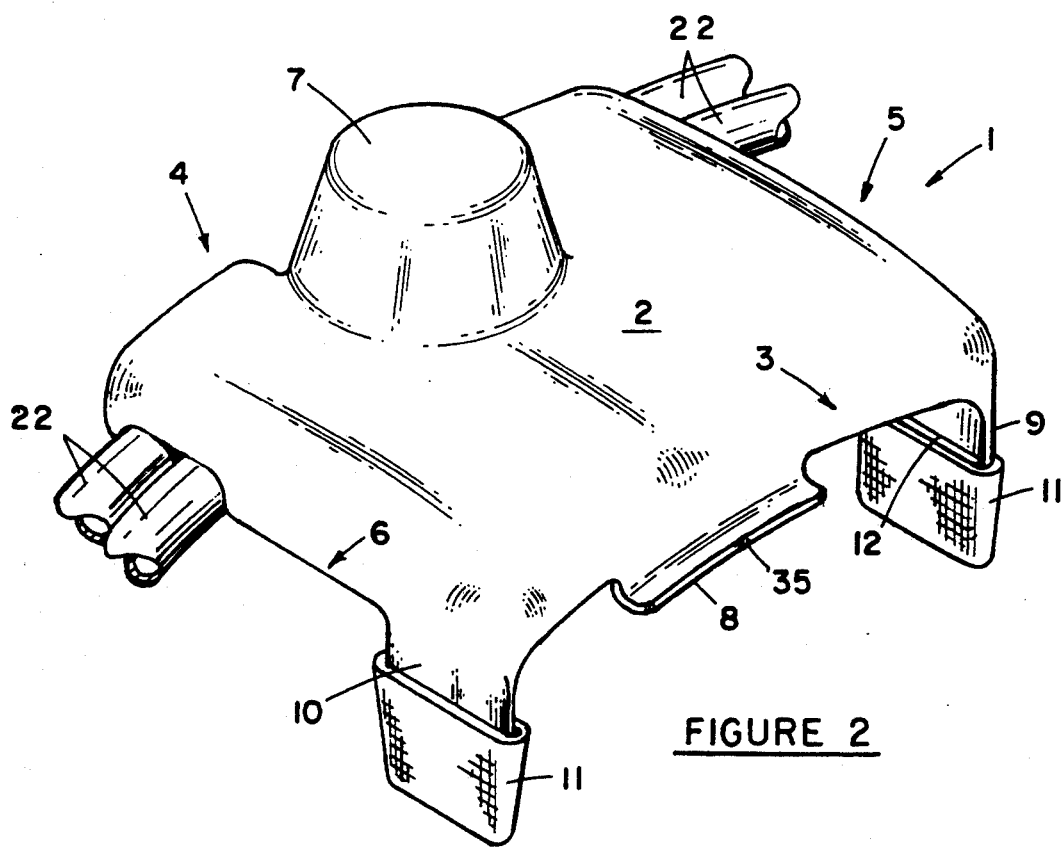
FIG. 2 is a pictorial view of the shield of FIG. 1 taken from the forehead edge of the shield.

In the figures, like numbers refer to like objects. In the figures some sections have been thickened for ease of illustration.

Referring now to FIGS. 1 through 4. Protective eye shield 1 has its principle elements formed of a semi flexible clear or tinted plastic material and is characterized by having a broad eye shielding central span 2 having a face side surface 32 and an outside surface 33. Eye shielding central span 2 is bounded on one side by a forehead edge 3, and on the opposite side by nose edge 4. Right side edge 5 and left side edge 6 span the distance between forehead edge 3 and nose edge 4. Edges 3,4,5, and 6 form a closed perimeter for central span 2.

Nose hood 20 is provided with flexible seal 21 which contacts the patient's nose, cheeks and upper lip to form a seal against the entry or loss of gases. Hood 20 is also provided with hoses 22 which carry inhalation gases to hood 20 and carry exhalation gases away from hood 20. Hoses 22 lie closely along the face of the patient and form an effective barrier to materials passing between the patients face and nose hood 20 or hoses 22.

Nose edge 4 of shield 1 is provided with hood index 7 which serves to index shield 1 to nose hood 20. Hood index 7 is hereshown as an integral part of shield 1 and index 7 is in the form of an inverted cup which approximates the shape of an inhalation gas providing nose hood 20 with which it cooperates and to which it indexes.

Forehead edge 3 has as a part thereof, forehead contacting surface 8 which is configured so as to rest comfortably against the patient's forehead 34. Forehead contacting surface 8 is in the form of a curved bar which projects from forehead edge 3 of shield 1 and the curve of the bar approximates the curve of the forehead 34 of a human head and the curve of the bar presents a smooth surface 35 that will rest comfortably upon the forehead of the patient.

Right side edge 5 and left side edge 6 are provided with right temple piece 9 and left temple piece 10 respectively. Temple pieces 9 and 10 serve to provide positional security to shield 1 relative to the face of the patient. The comfort of temple pieces 9 and 10 and the closeness of their fit is enhanced by the use of cushioning sleeves 11. As shown in the sectioned view of FIG. 4, cushioning sleeve 11 is constructed of a compressible resilient material such as elastic cotton or the like. Cushioning sleeves 11 engages the free ends 36 of temple pieces 9 and 10. Adjustment inserts 12, of folded cotton gauze or the like, are insertable into sleeve 11 on the face side of temple pieces 9 and 10. Inserts 12 serve to cushion the pressure of temple pieces 9 and 10 against the head of the patient, and also serve to insure a firm and secure fit of shield 1 with the head of the patient.

Shield 1 as disclosed above indexes to and cooperates with nose hood 20 to form an eye protection system for use during dental surgery when a patient is wearing an inhalation gas dispensing nose hood and access to the oral cavity is required.

Shield 1 can be joined to or combined with nose hood 20 by a number of convenient means.

Referring now to FIG. 5 wherein shield 1 at nose edge 4 and adjacent to hood index 7, is provided with a first Velcro (TM) fastening tape 19 and wherein nose hood 20 is provided with a second, mating Velcro (TM) fastening tape 19' at the intersection 14 of hoses 22 and nose hood 20. A similar set of tapes is provided to each side of index 7 and hood 20.

Figure 6:
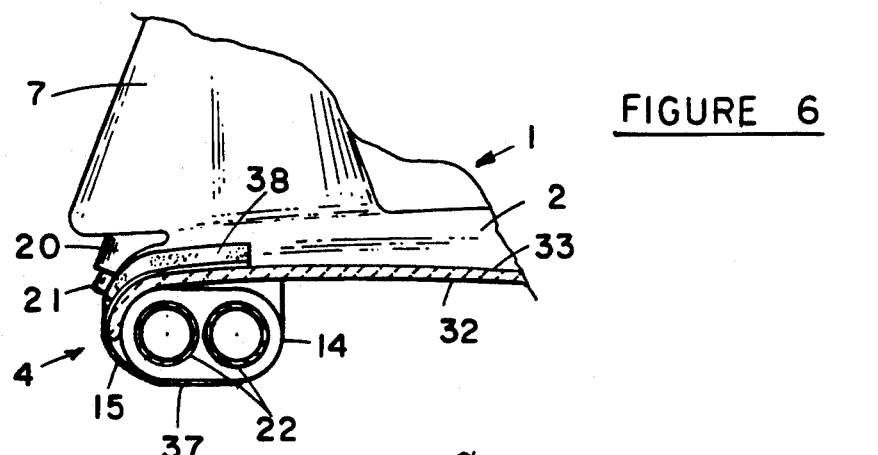
FIG. 6 is a partially sectioned elevational view of the nose edge of the shield of this invention showing a tape joinder means.

Referring now to FIG. 6 wherein shield 1 is provided at its nose edge 4 with adhesive tapes 15, one to each side of index 7, and which hingeably join shield 1 to intersection 14 of hoses 22 of nose hood 20. Tapes 15 serve to maintain the joinder of shield 1 with hoses 22 while permitting shield 1 to be raised to permit access to hood 20, or seal 21 or to blot perspiration from the patient's brow. Tapes 15 have first end segments 37 which are secured to intersection 14 of hoses 22 of nose hood 20 and second end segments 38 which are secured to shield 1 near nose edge 4.

Figure 7:
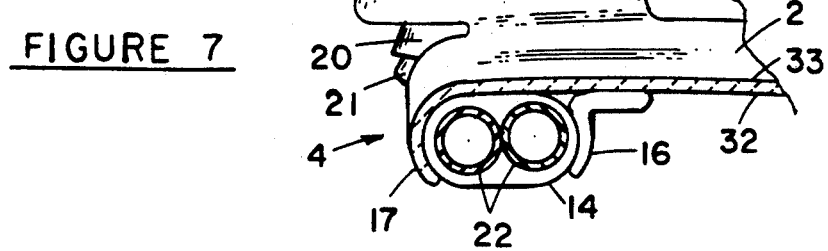
FIG. 7 is a sectioned elevational view of the nose edge of the shield of this invention showing a clip means of joinder.

Referring now to FIG. 7 wherein a mechanical clip 16 is secured near nose edge 4 of shield 1, one at each side of index 7, and the clip mechanically engages intersection 14 of hoses 22 of hood 20. Shield 1 has as a part of nose edge 4, a curved segment 17 which, in combination with mechanical clip 16, encompasses more than half of the perimeter of intersection 14 of hoses 22. To join shield 1 with nose hood 20 at intersection 14 of hoses 22, curved segment 17 and clip 16 are urged apart, in the maner that is customary in applying spring clips, and are passed, one to each side of intersection 14 of hoses 22 and allowed to return to their normal unstressed position, thereby mechanically joining shield 1 with intersection 14 of hoses 22. Clip 16 may be positioned so as to engage hoses 22 of nose hood 20 when it is seen as desirable to do so.

Figure 8:
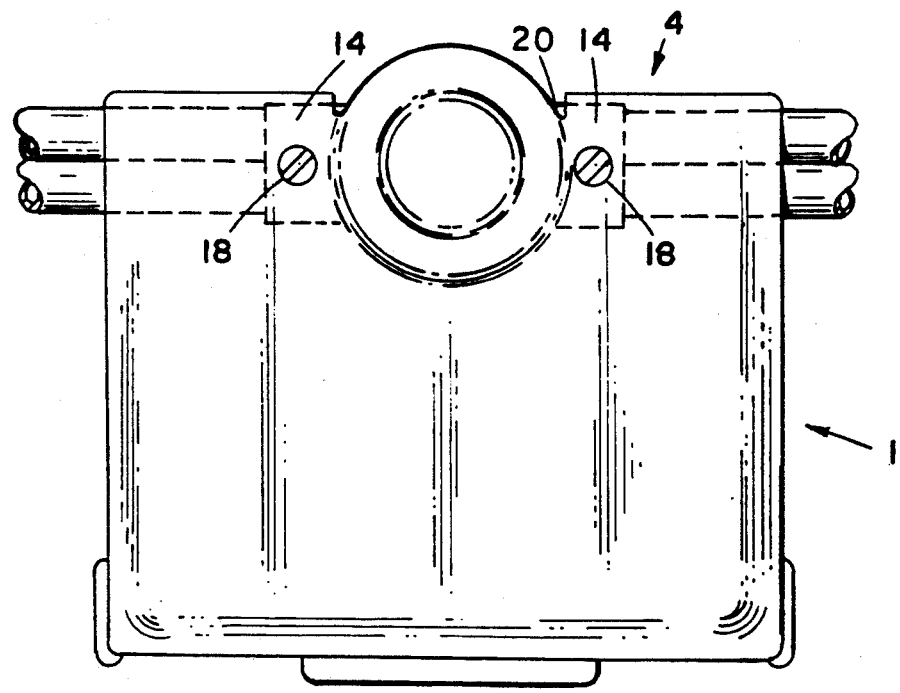
FIG. 8 is a plan view of the shield of this invention showing a threaded fastener means of joinder.

Referring now to FIG. 8 wherein shield 1 is shown as being joined with nose hood 20 by means of threaded fasteners 18 to form a substantially unitary structure. In some situations it will be desirable to have nose hood 20 and shield 1 combined to form a substantially unitary structure. Threaded fasteners 18 provide that utility while at the same time permitting the separation of shield 1 from hood 20 should it be desirable to do so. Threaded fasteners 18, which may be conventional screws, pass through shield 1 and are threadably engaged into intersection 14 of nose hood 20.

Preferred embodiments of this invention have been disclosed and discussed above. Many variants and combinations of the elements of the invention will suggest themselves to one skilled in the art. Such variants might include those necessary for the adaption of the shield of this invention to the specific geometries of a specific manufacture of nose hood. Disclosure and discussion of all possible combinations and variants of the elements of this invention would greatly multiply the drawings and cause the specifications to become prolix. Therefore, the invention should not be limited to the embodiments disclosed above, but be limited only by the appended claims and all equivalents thereto that would become obvious to one skilled in the art.

I claim:

1. An eye shield, in combination with an inhalation gas providing nose hood and comprising;
   1) a substantially one piece eye shield structure of a semi-flexible clear plastic material,
   2) said structure having a broad eye protecting central span,
   3) said central span having a perimeter bounded on one side by a forehead edge, and bounded on the opposite side by a nose edge, and having a first side edge and a second side edge, and the first side edge and the second side edge span the distance between the forehead edge and the nose edge, one to each side of the central span to form a closed perimeter about the central span, and
   4) the forehead edge is provided with an integral forehead contacting surface that is configured to rest comfortably on a human forehead, and
   5) the side edges have projecting therefrom temple pieces, having free ends and which are configured so as to contact with and index to the temple area of a human head, and
   6) the eye shield is fixedly secured to an inhalation gas providing nose hood by means of threaded fasteners that pass through the face shield and threadably engage the nose hood.

2. The shield of claim 1 wherein the temple pieces are provided with cushioning sleeves of resilient elastic material which enclose the free ends of the temple pieces and the cushioning sleeves are configured to receive adjustment inserts that pad the free ends of the temple pieces and also serve as a means for adjusting the fit of the shield at the temple area of the head of the patient.

3. An eye shield for use with an inhalation gas providing nose hood having gas carrying hoses and comprising:
   1) a substantially one piece structure of a semi-flexible clear plastic material, 2) said structure having a single broad eye protecting central span, having a face side surface and an outside surface,
3) said central span having a perimeter bounded on one side by a forehead edge, and bounded on the opposite side by a nose edge, and having a right side edge and a left side edge, and the right side edge and the left side edge span the distance between the forehead edge and the nose edge, one to each side of the central span to form a closed perimeter about the central span, and
4) the forehead edge is provided with an integral forehead contacting surface that is configured to rest comfortably on a human forehead, and
5) a nose hood index is formed in the central span near the nose edge of the span, and the nose hood index is configured so as to receive and index to the inhalation gas providing nose hood,
6) the side edges have projecting therefrom, temple pieces, having free ends, and which are configured so as to contact with and index to the temple area of a human head, and
7) wherein the nose edge of the shield has secured to its face side surface near the nose edge of the shield, mechanical clip members, one to each side of the nose hood index, and the clip members, in combination with a curved segment of the nose edge of the shield embrace more than 50 percent of the transverse perimeter of the hoses of the nose hood and thereby form a resilient releasable mechanical engagement between the shield and the nose hood.

4. The shield of claim 3 wherein the temple pieces are provided with cushioning sleeves of resilient elastic material which enclose the free ends of the temple pieces and the cushioning sleeves are configured to receive adjustment inserts that pad the free ends of the temple pieces and also serve as a means for adjusting the fit of the shield at the temple area of the head of the patient.

5. The shield of claim 3 wherein the nose hood index is formed as an integral part of the shield and the index is in the form of an inverted cup which approximates the shape of the inhalation gas providing nose hood with which it cooperates and to which it indexes.

6. The shield of claim 3 wherein the forehead contacting surface is in the form of a curved bar which projects from the forehead edge of the shield and the curve of the bar approximates the curve of the forehead of a human head and the curved bar presents a smooth surface that will rest comfortably upon the forehead of a patient when the shield is in place on the patient.

7. An eye shield for use with an inhalation gas providing nose hood having gas carrying hoses and comprising:
1) a substantially one piece structure of a semi-flexible clear plastic material,
2) said structure having a single broad eye protecting central span, having a face side surface and an outside surface,
3) said central span having a perimeter bounded on one side by a forehead edge, and bounded on the opposite side by a nose edge, and having a right side edge and a left side edge, and the right side edge and the left side edge span the distance between the forehead edge and the nose edge, one to each side of the central span to form a closed perimeter about the central span, and
4) the forehead edge is provided with an integral forehead contacting surface that is configured to rest comfortably on a human forehead, and
5) a nose hood index is formed in the central span near the nose edge of the span, and the nose hood index is configured so as to receive and index to the inhalation gas providing nose hood,
5) the side edges have projecting therefrom, temple pieces, having free ends, and which are configured so as to contact with and index the temple area of a human head, and
7) wherein the shield is provided with a first hook and loop tape fastener, secured to the face side surface of the shield, and the inhalation gas providing hood is provided with a mating, second hook and loop tape fastener and the shield is rendered detachably joinable to the hood by means of joining said first and second hook and loop tape fasteners.

8. An eye shield for use with an inhalation gas providing nose hood having gas carrying hoses and comprising:
1) a substantially one piece structure of a semi-flexible clear plastic material,
2) said structure having a single broad eye protecting central span, having a face side surface and an outside surface,
3) said central span having a perimeter bounded on one side by a forehead edge, and bounded on the opposite side by a nose edge, and having a right side edge and a left side edge, and the right side edge and the left side edge span the distance between the forehead edge and the nose edge, one to each side of the central span to form a closed perimeter about the central span, and
(4) the forehead edge is provided with an integral forehead contacting surface that is configured to rest comfortably on a human forehead, and
5) a nose hood index is formed in the central span near the nose edge of the span, and the nose hood index is configured so as to receive and index to the inhalation gas providing nose hood,
6) the side edges have projecting therefrom, temple pieces, having free ends, and which are configured so as to contact with and index to the temple area of a human head, and
7) wherein the shield is hingeably joined to the nose hood hoses by means of strips of adhesive tape having a first end segment and a second end segment and the first end segment is secured to the hoses of the nose hood and the second end segment is attached to the nose edge of the shield so as to hingeably join the shield to the hoses of the inhalation gas providing nose hood.

* * * * *